US005774213A

United States Patent [19]
Trebino et al.

[11] Patent Number: 5,774,213
[45] Date of Patent: Jun. 30, 1998

[54] TECHNIQUES FOR MEASURING DIFFERENCE OF AN OPTICAL PROPERTY AT TWO WAVELENGTHS BY MODULATING TWO SOURCES TO HAVE OPPOSITE-PHASE COMPONENTS AT A COMMON FREQUENCY

[76] Inventors: Rick P. Trebino, 425 Mulqueeney Dr., Livermore, Calif. 94550; Nicholas M. Sampas, 806 Fremont St., Menlo Park, Calif. 94025; Eric K. Gustafson, 835 Webster St., Apt. E, Palo Alto, Calif. 94301

[21] Appl. No.: 518,427

[22] Filed: Aug. 23, 1995

Related U.S. Application Data

[63] Continuation-in-part of Ser. No. 426,790, Apr. 21, 1995, abandoned.

[51] Int. Cl.$^6$ ..................................................... G01N 21/31
[52] U.S. Cl. .............................. 356/320; 356/41; 356/408
[58] Field of Search ............................. 356/41, 321, 408, 356/320

[56] References Cited

U.S. PATENT DOCUMENTS

| | | | |
|---|---|---|---|
| 2,601,182 | 6/1952 | Tyler | 356/321 |
| 3,332,313 | 7/1967 | Batson | 356/408 |
| 3,472,594 | 10/1969 | Hughes et al. | 356/320 |
| 3,647,299 | 3/1972 | Lavallee | 356/41 |
| 3,799,672 | 3/1974 | Vurek | 356/41 |
| 4,183,669 | 1/1980 | Doyle | 356/346 |
| 4,305,659 | 12/1981 | Bilstad et al. | 356/40 |
| 4,350,441 | 9/1982 | Wicnienski | 356/408 X |
| 4,529,308 | 7/1985 | Rife | 356/323 |
| 4,948,248 | 8/1990 | Lehman | 356/41 X |
| 5,028,787 | 7/1991 | Rosenthal et al. | 250/341 |
| 5,059,027 | 10/1991 | Roesler et al. | 356/346 |
| 5,137,023 | 8/1992 | Mendelson et al. | 128/633 |
| 5,184,193 | 2/1993 | LeFebre | 356/319 |
| 5,206,701 | 4/1993 | Taylor et al. | 356/325 |
| 5,245,406 | 9/1993 | Masutani | 356/346 |
| 5,251,008 | 10/1993 | Masutani | 356/346 |
| 5,349,952 | 9/1994 | Carthy et al. | 356/41 X |

OTHER PUBLICATIONS

Kelleher, Joseph F., "Pulse Oximetry," Little, Brown and Co., 1989, pp. 37–62.

*Primary Examiner*—Vincent P. McGraw
*Attorney, Agent, or Firm*—Townsend and Townsend and Crew LLP

[57] ABSTRACT

A technique for making precise spectrophotometric measurements illuminates a sample with two or more modulated light sources at two or more, typically closely spaced, wavelengths. Light from the sources is combined, homogenized, and directed to the sample, and the light from the sample is collected and detected by a photodetector. The optical output powers of two sources are modulated with the same periodicity and with a reversed amplitude. Variations in the concentrations of species in the sample affect the modulation amplitude representing the sum of the optical powers from two sources in such a way as to produce an output signal. That output signal, based on an electrical component varying with a periodicity at the fundamental frequency, provides a measure of the difference in the transmissions (or other optical properties) of the sample at the two wavelengths. Feedback methods, such as null-point detection, provide stable, sensitive measurements. Wavelength-division multiplexing—required for simultaneous measurements at many wavelengths—is achieved by modulating different pairs of sources at different frequencies.

11 Claims, 11 Drawing Sheets

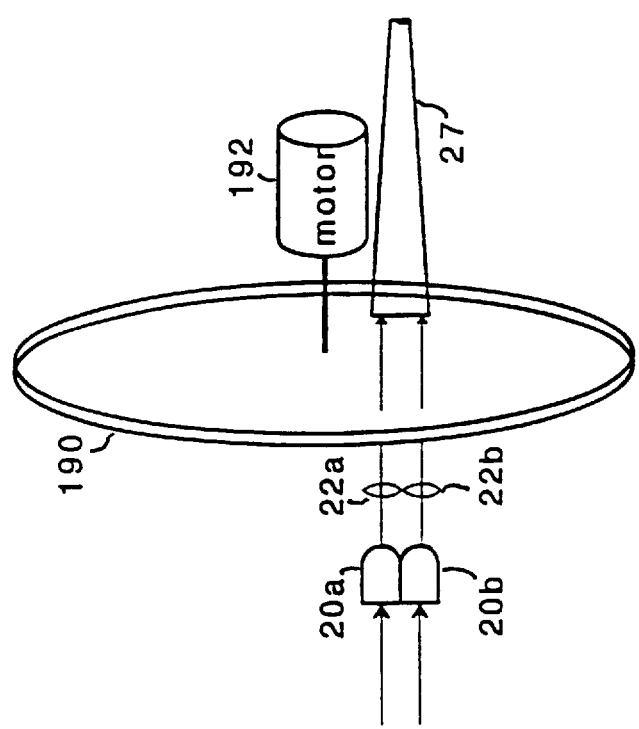

TECHNIQUES FOR MEASURING DIFFERENCE OF AN OPTICAL PROPERTY AT TWO WAVELENGTHS BY MODULATING TWO SOURCES TO HAVE OPPOSITE-PHASE COMPONENTS AT A COMMON FREQUENCY

CROSS-REFERENCE TO RELATED APPLICATION

This application is a continuation-in-part of U.S. application Ser. No. 08/426,790, filed Apr. 21, 1995, now abandoned, which application is incorporated herein by reference for all purposes.

BACKGROUND OF THE INVENTION

The present invention relates generally to optical spectroscopy, and more specifically to a spectrophotometer suitable for performing non-invasive measurement of metabolic analytes and for determining characteristics of substances in the solid, liquid, and gas phases in other, e.g. industrial settings.

A new generation of medical and industrial diagnostic instruments based upon optical spectroscopy, typically in the near infrared region, enable non-invasive measurements of metabolic constituents in the body and of a wide range of parameters of inanimate objects and fluids. These diagnostic techniques involve measuring the absorbance, scatter, transmission, or reflection spectra of living tissue non-invasively, and hence conveniently and painlessly. Already, optical diagnostics exist or are under active development for measuring a wide variety of important metabolic quantities, including oxygen saturation of hemoglobin, body fat, cholesterol, triglycerides, bilirubin, and glucose. In addition, similar optical diagnostic techniques are important in agriculture, semiconductor processing, petroleum processing and refining, combustion diagnostics and other fields.

To extract information relating to metabolic analyte concentrations or material properties from raw spectral measurements, one uses any one of a variety of inversion techniques. A specific theoretical or empirical model may be known. More commonly, one uses a technique known as chemometric-multivariate calibration, or "chemometrics". Chemometrics is a class of sophisticated mathematical algorithms that reduce large spectral calibration matrices to a mathematical model that can be applied to new spectral data to determine the concentrations of various constituent analytes. Commonly used chemometric algorithms include: partial least squares (PLS), multiple linear regression (MLR), and principal component regression (PCR). In addition, another method involves the use of neural networks. This latter method is especially useful when nonlinear behavior occurs, and the linearity assumption of chemometrics is no longer valid.

For all but a few simple diagnostics, extremely sensitive measurements are required for reasonably reliable measurements. This is especially the case, in the example of in vivo glucose measurement where the absorbance changes due to glucose are weak. Unfortunately, devices with sufficient sensitivities for measurement of these analytes are prohibitively expensive (typically exceeding $30,000). As a result, diabetics stand little chance of home glucose monitoring with a non-invasive optical device with existing technology. In general, when many species contribute to the absorption signal, high sensitivity is required. Indeed, the greater the sensitivity of the spectrophotometer, the more species may be measured, and, in particular, trace species or very weakly absorbing species may be measured.

Currently available spectrophotometers fall into two general classes, (1) those designed for general optical spectroscopy and (2) those designed specifically for non-invasive clinical applications. The devices in the first class include both Fourier-transform spectrometers (FTS's) and frequency-domain grating-tuned spectrophotometers (GTS's). Both these types of instruments are engineered for maximal sensitivity and high resolution, and hence they are quite costly. An FTS involves a highly sensitive, precisely aligned optical interferometer, the optical pathlength of which is scanned during a measurement. It also requires a powerful computer that can rapidly calculate fast Fourier transforms (FFT's). Because of their complexity, FTS's are likely to remain expensive. GTS's are also finely tuned instruments with high resolution determined by precisely scanning (to less than a microradian) a finely ruled diffraction grating. As a result, high-resolution GTS's will undoubtedly remain expensive as well. In addition, due to their need for precise alignment, both of these devices tend to be heavy and not portable.

The second class of spectrophotometers, which will be referred to as "portable" spectrophotometers, offer only limited spectral resolution and hence typically only involve measurements at a modest number of wavelengths. See, for example, U.S. Pat. No. 5,028,787 to Rosenthal et al. Such devices are useful for specific diagnostic analyses, generally of a solid or liquid-phase sample, in which only low resolution is required, and typically, the number of required wavelengths is limited and often known in advance. These devices typically require less than $1/1000$th the resolution of the general-spectroscopic class of spectrophotometers. Indeed, simple portable devices that measure the most strongly absorbing quantities in tissue, such as the oxidation of hemoglobin, require as few as two wavelength measurements and are in fact inexpensive. See, for example, J. F. Kelleher, "Pulse Oximetry," J. Clinical Monitoring, Vol. 5, #1, pp. 37–62 (1989). More commonly, industrial measurements and human body analyte diagnostics require between 10 and 40 wavelengths to provide sufficient information due to the many interfering absorptions of other species in the range of physiological or industrial interest. In addition, such measurements are possible only when the signals are relatively strong and the number of competing species is limited. Most important clinical and industrial problems, however, involve much more weakly absorbing substances. As a result, significantly higher sensitivity is also required.

Current portable spectrophotometers have not only very low resolution, but also very low sensitivity. There are a variety of reasons for this. One is the common use of pulsed sources, which are substantially noisier than continuous-wave sources. Another is the use of sequential measurements of the absorbances at the various wavelengths of interest, thus allowing drift to introduce error into the measured spectrum. In addition, no attempt is made to take advantage of clever noise-reduction techniques used in other fields (such as null-point detection). Often devices analogous to available high-resolution devices are used, and hence tend to be both expensive and heavy. The state of art in noise reduction in grating-type spectrophotometers is nicely reviewed in U.S. Pat. No. 5,206,701 to Taylor et al.

Many applications also require real-time monitoring of the spectral properties of a sample. Unfortunately, standard methods are too slow to achieve rapid measurements because they involve slowly scanning the wavelength (as in GTS's and in devices in which the many sources are sequentially pulsed) or scanning an optical delay path (as in FTS's). These devices, are therefore too slow for many real-time monitoring applications, which involve temporally resolving, for example, changes in blood volume due to the heart pulse. In addition, most spectrophotometers make DC measurements. DC measurements integrate noise at low frequencies, and hence are extremely sensitive to low-frequency or "1/f" noise.

The most common problem with spectrophotometers is that spectra tend to vary from measurement to measurement due to drifts associated with the sources, electronics, and detector within the instrument. Specifically, two spectra taken only seconds apart in an unchanging medium may have similar spectral characteristics, but are typically offset somewhat relative to each other. Consequently, one spectrum will appear slightly more (or less) absorbing than another at all wavelengths. Similarly, there often occur slow baseline shifts across a single spectrum. Uncorrected, the use of such baseline-shifted spectra generally yields erroneous or poor quality results. Such instrument drifts therefore limit sensitivity and hence the diagnostic power of the technique. The only devices for which source drift is not a serious limitation are FTS's, but, as mentioned, their alignment-sensitivity, weight, and high cost make them unsuitable for small-scale medical, clinical, quality-control, or regulatory applications.

To minimize this problem, it is common practice to subtract the intensity of a reference beam that takes an independent path that does not involve passing through the sample. This method is discussed in U.S. Pat. No. 5,206,701 to Taylor et al., U.S. Pat. No. 5,184,193 to LeFebre, and U.S. Pat. No. 4,529,308 to Rife. U.S. Pat. No. 4,183,669 to Doyle discusses the use of a reference beam in a Fourier-transform spectrophotometer. The use of a reference beam in this manner is helpful but it still does not solve the problem of different drifts in the components of the two different light paths.

An additional method that addresses the latter problem is the normalization of the spectrum by subtracting off the absolute transmission value at some reference wavelength. Unfortunately, this approach is limited because drift can occur in the time interval between the desired measurement and the reference measurement. A better method, one also commonly used, is to compute the first or second derivative of a spectrum with respect to wavelength before using it to determine a useful value of the desired quantity. In this way, consecutive measurements are subtracted, and reliance on a single reference measurement for the entire spectrum is not necessary.

Taking the first derivative subtracts off any constant background, and taking the second derivative subtracts off a linearly sloped background. Typically, the useful information contained in a spectrum is unaffected by these transformations, but the noise associated with the individual wavelength measurements increases with each higher order of derivative. This is because the derivative is a difference between approximately equal adjacent spectral values, and each time such a difference is computed, the noise increases significantly. It would be much better to somehow measure the first or second derivative directly as a single measurement, and not as a difference between two measurements (as in the first derivative) or worse, as a difference of differences (as in the second derivative).

Most commonly, however, the derivative spectra are computed, and not measured directly: the transmissions measured at all wavelengths are digitized, and the differences are computed digitally. Unfortunately, this method has limited sensitivity due to noise in each measurement and the quantization error in the digitization. If, for example, an analog-to-digital converter (ADC) has 14 bits (that is, about 0.01% accuracy) and the difference between the transmissions at neighboring wavelengths is about 0.01%, then the error in the derivative measurements is on the order of 100%. Measurements of the second derivative are even more problematic, and, in this example, would be meaningless.

An array of next-generation medical and industrial diagnostics applications will become possible as greater sensitivity and more stable and more precise spectrophotometers become feasible and economical. Many other fields, such as process control and environmental safety, will benefit, as well.

SUMMARY OF THE INVENTION

The present invention provides a technique for making precise spectrophotometric measurements suitable for use in connection with non-invasive monitoring of human metabolic analytes and industrial products. The invention achieves low cost and very high sensitivity while allowing the extraction of nearly drift-free derivative spectra using only a single detector. Derivative measurements are made at all wavelengths simultaneously and without the need to compute a difference.

Broadly, the invention contemplates illuminating a sample with two or more independently modulated light sources at two or more, typically closely spaced, wavelengths. Light from the sources is combined, homogenized, and directed to the sample, and the light from the sample is collected and detected by a photodetector. The light from the sample may be reflected, transmitted, or scattered. The optical output powers of two sources, typically adjacent in wavelength, are modulated with the same periodicity and with a reversed amplitude (opposite sign) so as to have a common frequency component at an electrical frequency, but with opposite-phase AC intensity components for the two sources.

Variations in the concentrations of species in the sample affect the modulation amplitude representing the sum of the optical powers from two sources in such a way as to produce an output signal. That output signal, based on an electrical component varying with a periodicity at the fundamental frequency, provides a measure of the difference in the transmissions (or other optical properties) of the sample at the two wavelengths. From one such two-wavelength measurement the relative concentration of one species can be measured (in the absence of interfering species). In principle, each additional wavelength allows one additional species to be measured.

Thus, the invention recognizes that medical and industrial diagnostics require high sensitivity but typically without the requirement of high resolution (since solid- and liquid-phase absorptions are inherently spectrally broad). In view of this, the invention is able to combine a number of techniques that have previously been regarded as inappropriate in the context of spectrophotometers. These techniques, which include instantaneous background subtraction and derivative measurement, phase-sensitive detection, null-point detection and frequency-division multiplexing, provide low-cost, high-sensitivity, low-noise, low-drift spectral measurements.

A further understanding of the nature and advantages of the present invention may be realized by reference to the remaining portions of the specification and the drawings.

BRIEF DESCRIPTION OF THE DRAWINGS

FIG. 10 is a schematic of an alternative tunable light source utilizing a graded interference filter which makes the two-wavelength null-point technique work as a first derivative spectrometer.

DESCRIPTION OF SPECIFIC EMBODIMENTS

Two-Wavelength Embodiment without Feedback

Figure 1:
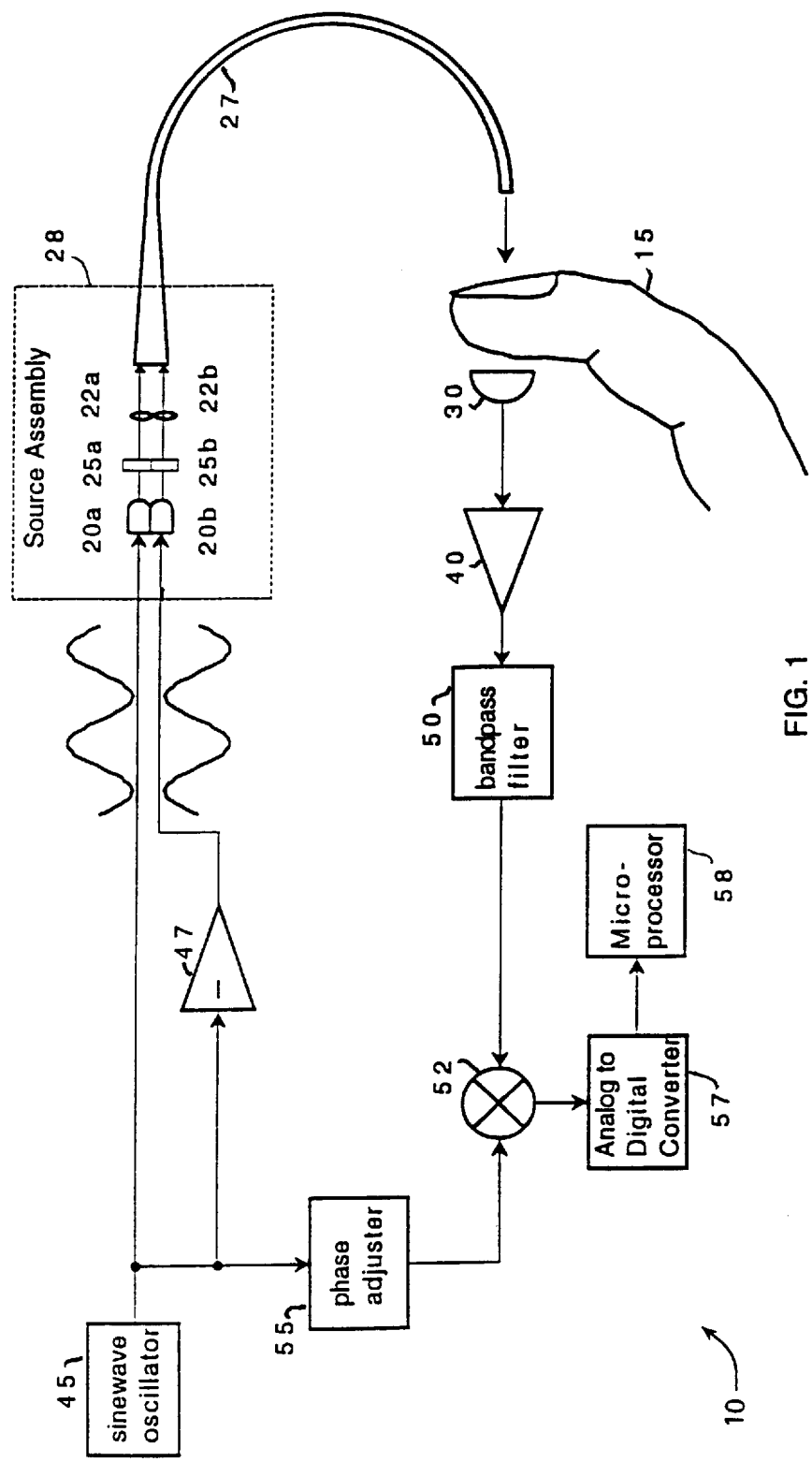
FIG. 1 is a schematic of an embodiment of the invention using two sources and no feedback.

FIG. 1 is an optical and electrical schematic of a system 10 according to a first embodiment of the invention. The purpose of the system is to determine the difference in the transmission (or other optical property) of light at two wavelengths on encountering a sample, shown as a human finger 15.

Light at the two wavelengths is provided by first and second amplitude modulated sources 20a and 20b, which in the specific embodiment are light-emitting diodes (LEDs). Light from LEDs 20a and 20b is directed through respective lenses 22a and 22b and through respective filters 25a and 25b to a beam homogenizer 27. The combination of sources, filters, and lenses can be considered a source assembly 28.

The need for filters depends on the bandwidth of the sources and the wavelength separation of the two sources. In some embodiments, a typical wavelength spacing is on the order of 5–10 nm. Since LEDs typically have a bandwidth on the order of 20 nm, the filters should have respective bandpass widths on the order of 5–10 nm. Laser diodes may also be used, and, due to their narrower bandwidth (say less than 0.1 nm), would not need to be used in conjunction with filters. It would be necessary to choose the proper laser diode wavelengths. There may be some applications where the wavelengths are sufficiently separated that filters are not necessary, even if LEDs are used.

LEDs that operate at room temperature are available in the visible and near infrared ranges, most commonly in the 600–1000 nm range and at wavelengths of 1300 nm and 1550 nm, the latter two wavelengths being in wide use in fiber optic communication systems.

The light from the homogenizer encounters the sample, and is detected by a photodetector 30. The photodetector transforms optical power to an electrical signal (voltage or current), which is amplified by a preamplifier 40.

Amplitude modulation of the sources is effected by an oscillator 45, having a fundamental frequency $\Omega$, typically in the range from 1 kHz to 1 MHz. The oscillator drives source 20a with a modulation of one phase and drives source 20b through an inverting amplifier 47 to provide modulation with the opposite phase. The waveforms representing each of the signals are shown schematically along their respective signal lines. The two sources are driven with respective average powers, $P_1$ and $P_2$ and modulation powers $\Delta P_1$ and $\Delta P_2$. The power of source 20a is $P_1 - \Delta P_1 \cos(\Omega t)$ while that of source 20b is $P_2 + \Delta P_2 \cos(\Omega t)$, whereupon the total power is $$P_{tot} = P_1 + P_2 + (\Delta P_2 - \Delta P_1) \cos(\Omega t)$$

Figure 2A:
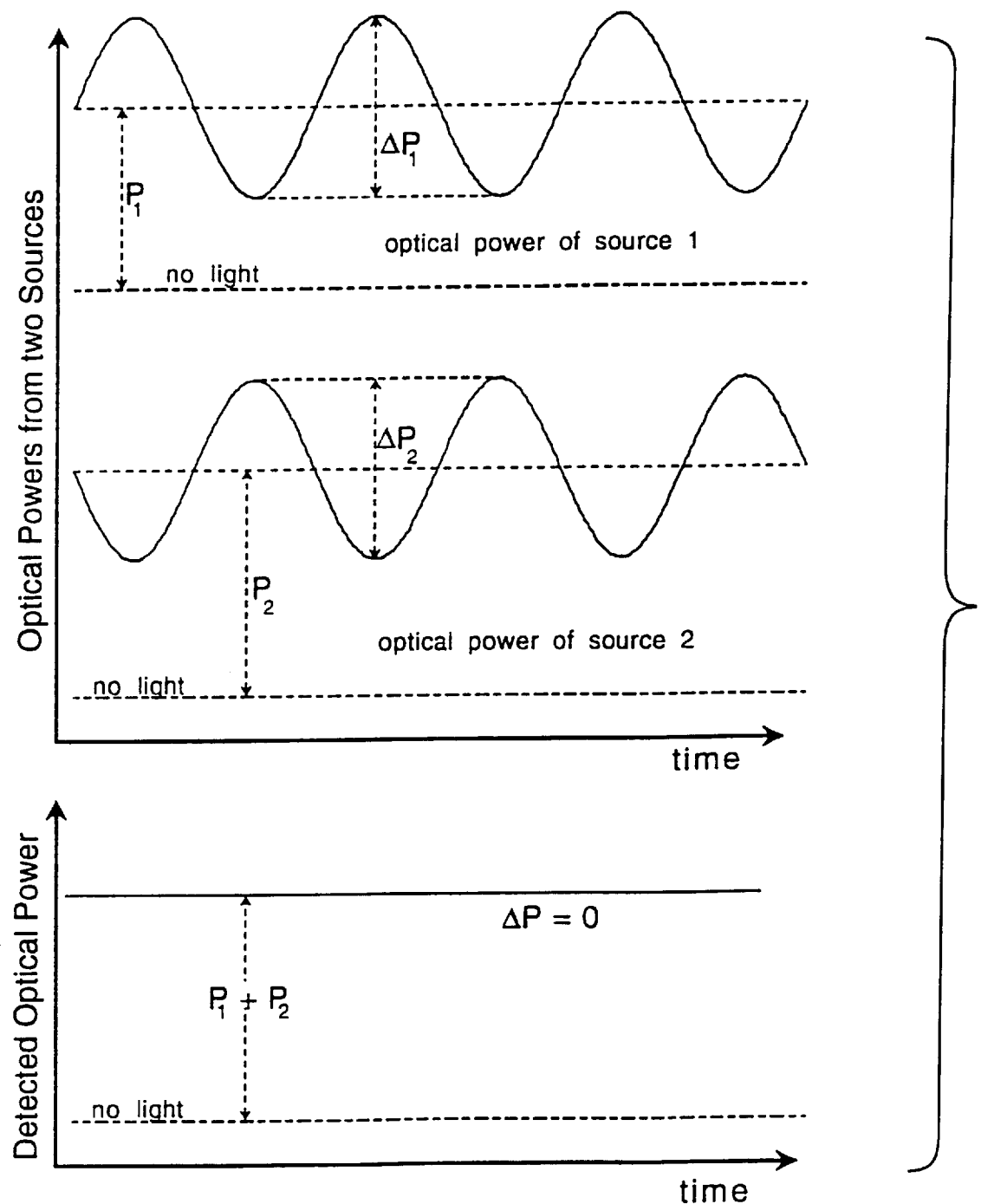
FIG. 2A shows plots of optical power at the two wavelengths and the total optical power before the light encounters the sample.

In this embodiment, the average powers and modulation powers are adjusted such that $\Delta P_1 = \Delta P_2$, so that $P_{tot}$ shows no modulation at the fundamental frequency. Similarly, the total power incident on the sample shows no modulation at the fundamental frequency. This is shown in FIG. 2A.

Figure 2B:
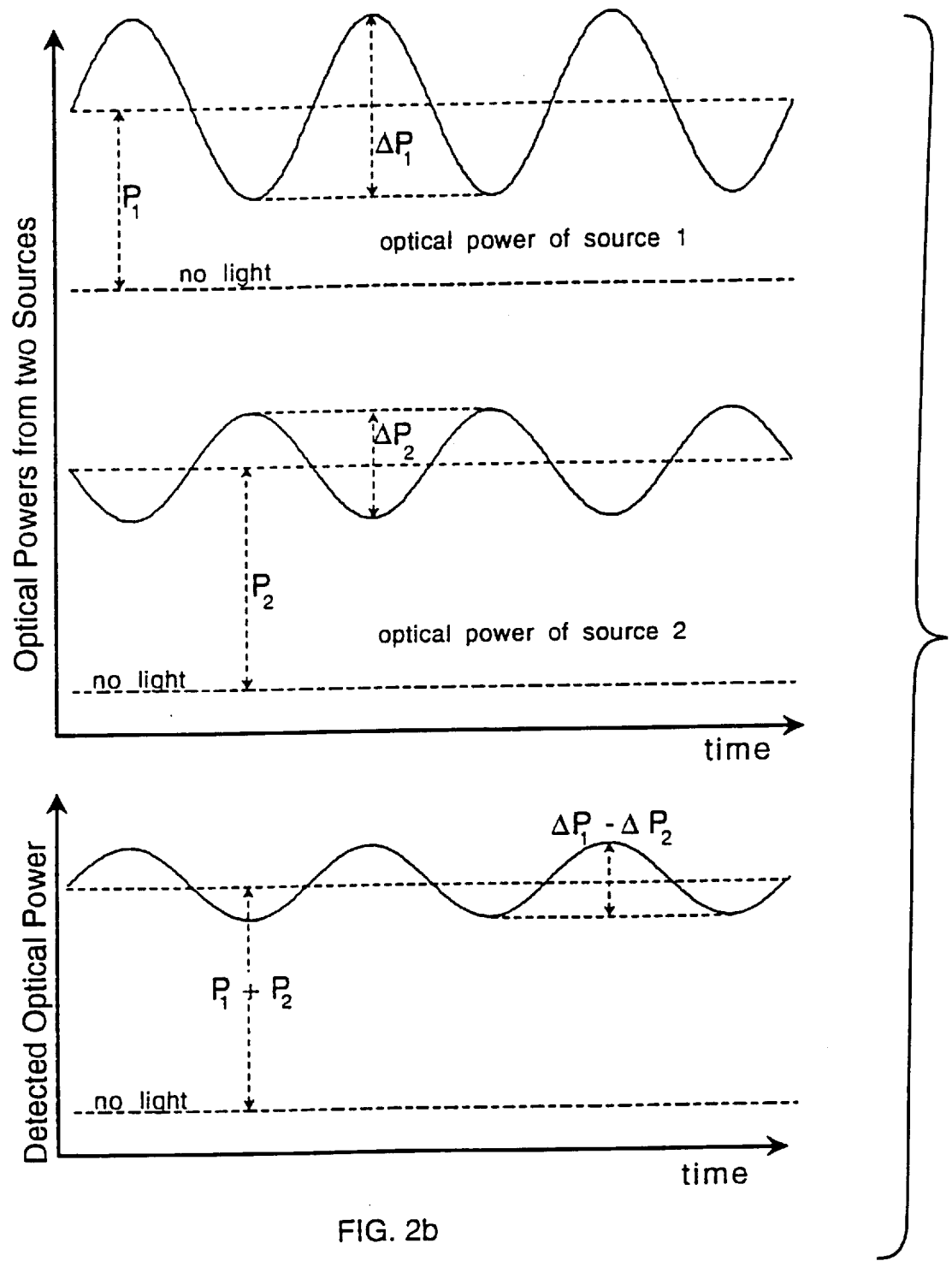
FIG. 2B shows plots of optical power at the two wavelengths and the total optical power after the light encounters the sample.

To the extent that the sample transmits both wavelengths of light equally, the light incident on the photodetector will not be modulated at the fundamental frequency. However, if, as shown in FIG. 2B, the sample transmits differently at the two wavelengths, the light incident on the photodetector will be modulated at the fundamental frequency in an amount proportional to the difference in the transmissions at the two wavelengths. Let $T(\lambda_1)$ be the transmission of the medium at $\lambda_1$ and $T(\lambda_2)$ be the transmission of the medium at $\lambda_2$. The transmitted power $p_{tot}^{trans}$ will then be:

$$\begin{aligned} P_{tot}^{trans} &= T(\lambda_1)(P_1 - \Delta P \cos(\Omega t)) + T(\lambda_2)(P_2 + \Delta P \cos(\Omega t)) \\ &= T(\lambda_1)P_1 + T(\lambda_2)P_2 + \Delta P(\lambda_2 - \lambda_1)T'(\bar{\lambda})\cos(\Omega t) \end{aligned}$$

where $\Delta P$ is the common value of the modulation power (since $\Delta P_1 = \Delta P_2$, the subscript is dropped) and the transmission spectral derivative, $T'(\bar{\lambda})$, is $$T'(\bar{\lambda}) = \frac{T(\lambda_2) - T(\lambda_1)}{\lambda_2 - \lambda_1}$$

where $\bar{\lambda}$ is the average of $\lambda_1$ and $\lambda_2$. Note that the modulated term (i.e., the term proportional to $\cos(\Omega t)$) is proportional to the desired quantity, the spectral derivative, $T'(\bar{\lambda})$, and the other factors in this term are easily measured. The extent of the modulation therefore provides a measure of the desired transmission difference. In addition, the phase of the modulation of the transmitted light provides the sign of transmission differences, which can be positive or negative.

Note that if $\lambda_2$ and $\lambda_1$ are nearby wavelengths (that is, the spectrum does not change significantly between $\lambda_1$ and $\lambda_2$), the quantity $T'(\bar{\lambda})$ will accurately indicate the transmission derivative. If the spectrum does change significantly between $\lambda_1$ and $\lambda_2$, the method is still valid; one is simply not measuring the derivative. The noise-reduction features continue to operate, but the derivative interpretation no longer applies.

An output signal representing this difference ($T'(\bar{\lambda})$) is generated using phase-sensitive detection. Specifically, the signal from preamplifier 40 is filtered by a bandpass filter 50 and mixed at a mixer 52 with a local oscillator signal derived from oscillator 45. The phase of the local oscillator signal is adjusted by a phase adjuster 55. Filter 50 suppresses all frequency components in the photodetector signal except the one at the fundamental, $\Omega$, which is converted to DC by mixer 52. This output signal is measured and constitutes a point in the derivative spectrum.

In order that useful information be derived from the voltage output signal of mixer 52, the signal may be output to a meter or converted to digital form by an analog-to-digital converter 57 and communicated to a processor 58 for further processing. In various embodiments described below, the meter or analog-to-digital converter and processor will not be illustrated, but it is to be understood that they will typically be present.

Two-Wavelength Embodiment with Feedback before Sample

Figure 3:
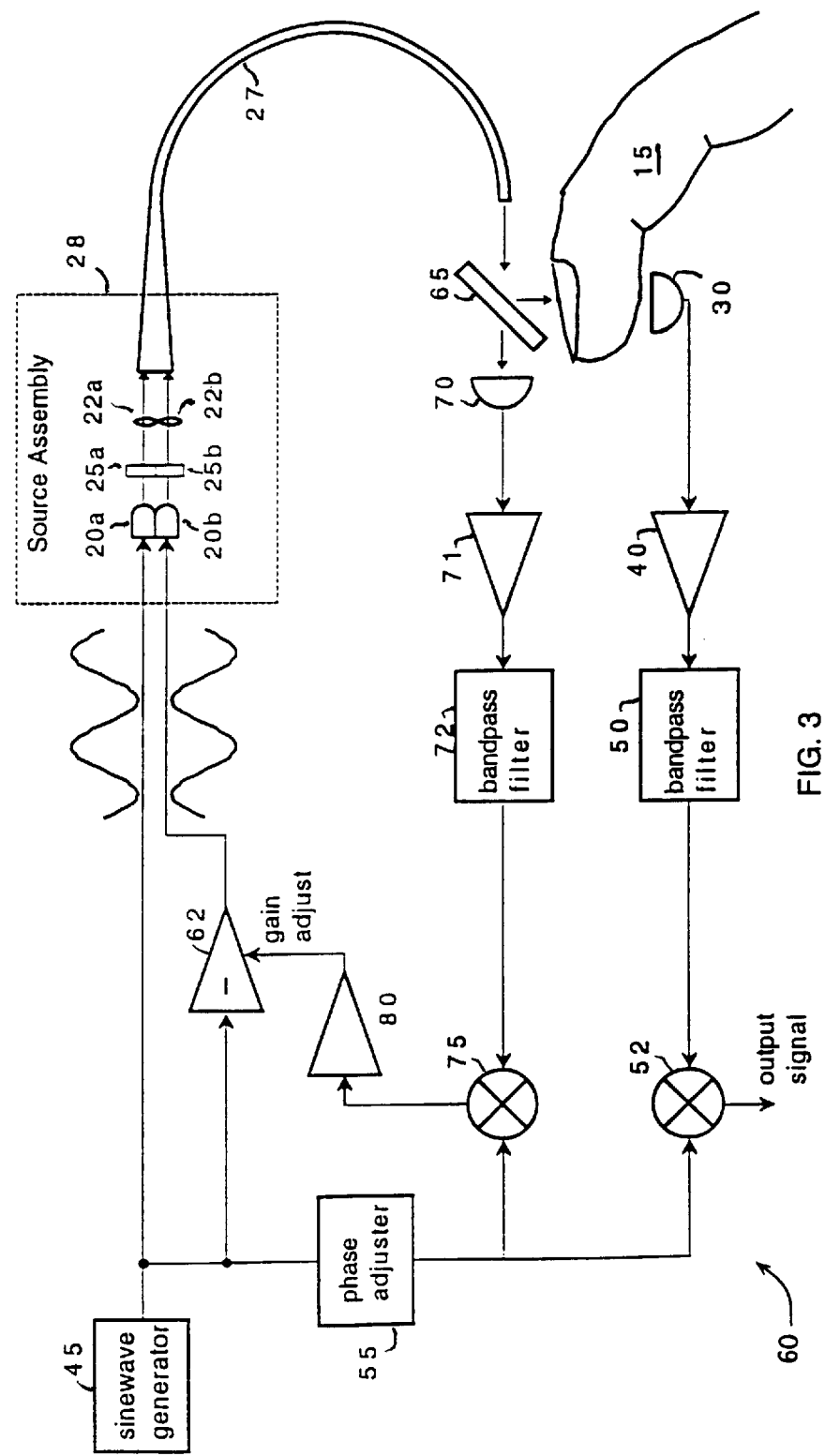
FIG. 3 is a schematic of an embodiment of the invention, which uses negative feedback to equalize the optical power of the two sources.

A potential source of error in this invention, as described so far, is drift in $\Delta P_1$ or $\Delta P_2$, which would yield spurious drifts in the measured derivative, $T'(\bar{\lambda})$. As a result, a number of embodiments of the invention use negative feedback in order to provide increased stability. (A particularly elegant and sensitive version of negative feedback, called null-point detection, will be discussed in the next section.) FIG. 3 is an optical and electrical schematic of a system 60 according to a further embodiment of the invention. Elements corresponding to those in FIG. 1 are denoted with the same reference numerals. This embodiment uses feedback to maintain equal modulation amplitudes for the power of the two sources. The apparatus includes the elements of the first embodiment, but includes additional elements as follows. Further, the inverting amplifier has a gain adjustment input, and is denoted by reference numeral 62.

A beamsplitter 65 intercepts the light emerging from beam homogenizer 27, and splits the light into two beams. One beam (comprising most of the light) passes through sample 15, and the other beam (comprising a few percent of the light) is used to generate a control signal for a servo loop. The difference in the two beam intensities is intended to compensate for the fact that the sample (here a finger) attenuates its beam. The additional elements include a photodetector 70, a preamplifier 71, a bandpass filter 72, and a mixer 75, which produce a signal proportional to the residual modulation of the light before it encounters the sample. This signal is fed back by a servo amplifier 80 to the gain adjustment input of inverting amplifier 62.

The output of mixer 52 provides the desired information regarding the sample as in the embodiment of FIG. 1, with the servo control ensuring that the residual modulation in the light after it penetrates the sample does not contain any contribution due to an inequality of the modulation amplitudes of the sources. The error signal can be nulled by feeding back to either of the complementary light sources or to both sources differentially.

Two-Wavelength Embodiment with Feedback after Sample ("Null-Point Detection")

Figure 4:
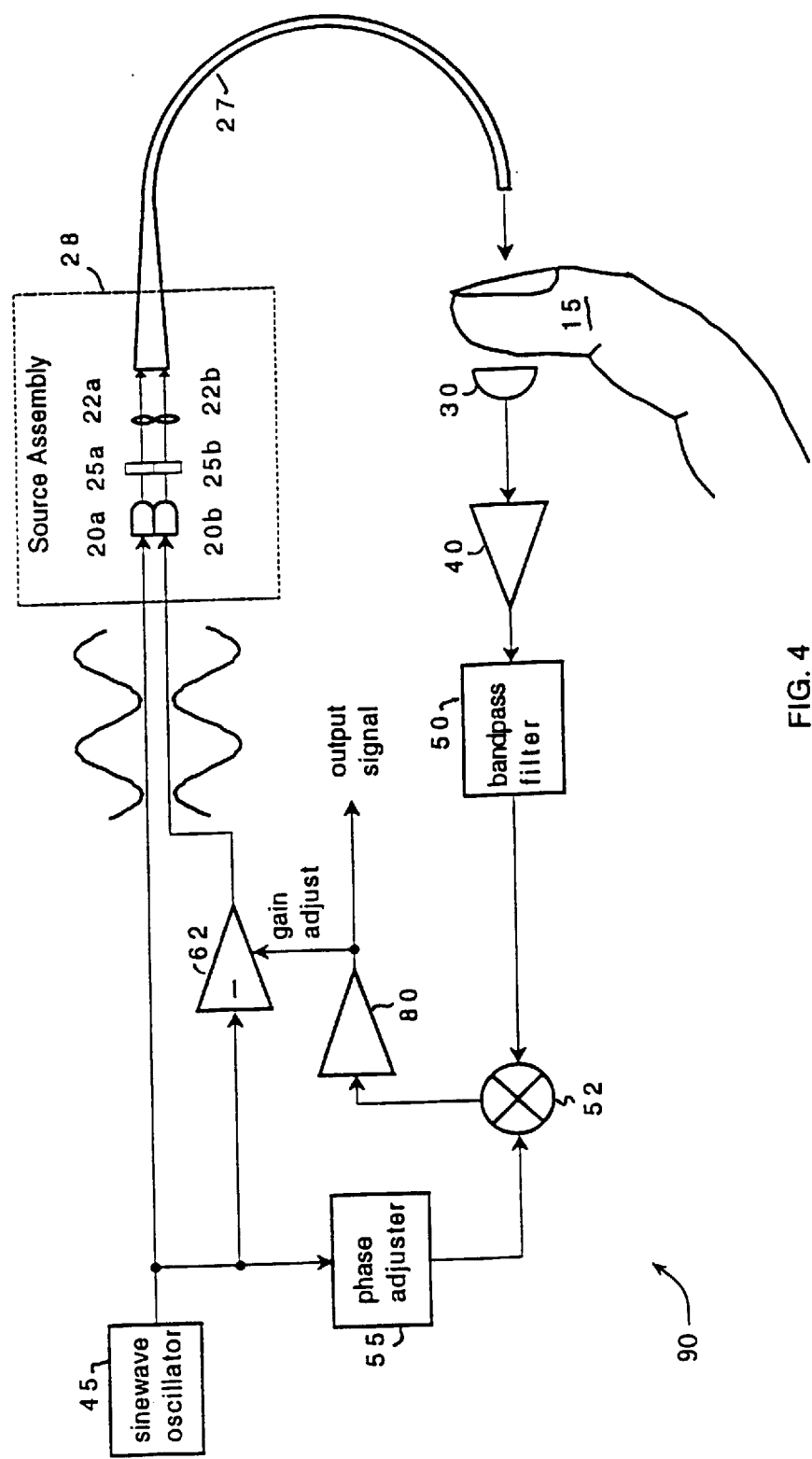
FIG. 4 is a schematic of an embodiment which uses negative feedback to null the residual modulation of the light from the sample.

FIG. 4 is an optical and electrical schematic of a system 90 according to a further embodiment of the invention. Elements corresponding to those in FIG. 1 are denoted with the same reference numerals. The sources are modulated so that the light leaving the sample has minimal residual modulation at the fundamental frequency. The imbalance in the modulation of the two sources represents the difference in the optical property of the sample at the two wavelengths.

This embodiment differs from the embodiment of FIG. 1 in that the output from mixer 52 is used as an error signal instead of the output signal containing the desired information. This error signal is used to impose a difference in the modulated intensities of the two sources in a manner tending to null out the fundamental component in the detector signal. In particular, the output from mixer 52 is communicated to servo amplifier 80, whose output is communicated to the gain adjustment input of inverting amplifier 62. The output from the servo amplifier now represents the desired transmission difference of the sample at the two source wavelengths.

This technique is referred to as "null-point detection," and it is in the most sensitive instruments ever developed, the class of scanned-probe microscopes (see H. K. Wickramasinghe, *Scientific American* Oct. '89 p.98) which are capable of spatial resolution on the order of an angstrom.

Feedback switching between Before Sample and After Sample

Figure 5:
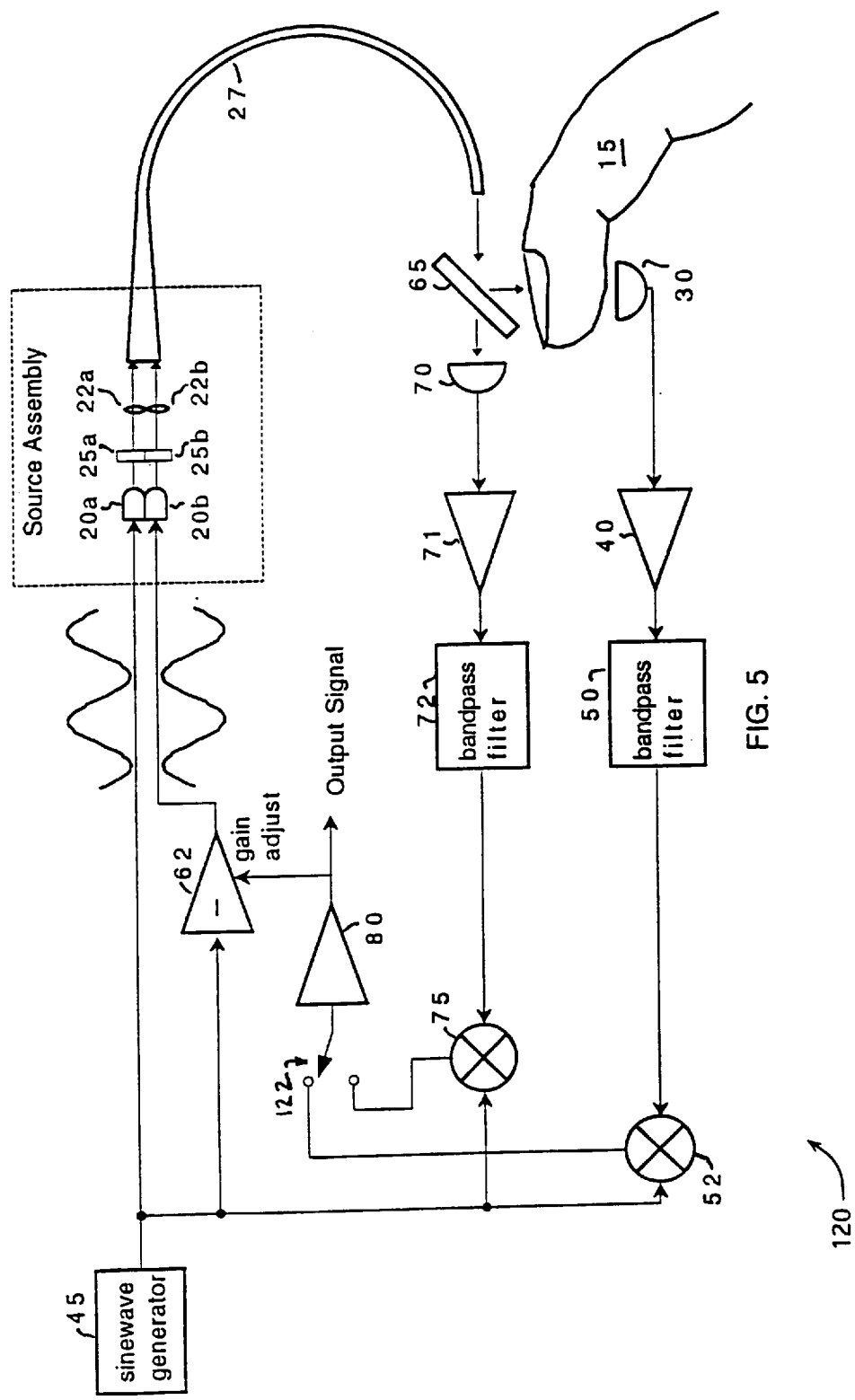
FIG. 5 is a schematic of an embodiment which switches the negative feedback between the regimes shown in FIGS. 3 and 4.

FIG. 5 is an optical and electrical schematic of a system 120 according to an embodiment in the error signal is alternately switched by a switch 122 between one signal derived from the light detected directly (as in FIG. 3) and another signal derived from the detector monitoring the light that probes the sample (as shown in FIG. 4). As such, the control loop closes alternately around the signal from source monitor detector 70 and the signal from sample detector 30. Both configurations are described in the above description of the two previous embodiments.

The control signal at the output of the servo amplifier 80 provides the output signal from which the spectral data are derived. The gain of the servo amplifier 80 may also be switched simultaneously with the signals to compensate for the differing signal strengths due to changes in the optical attenuation of the sample and differences in the beamsplitter efficiencies. The advantage of combining both embodiments in this way is that the time-varying effects of drifts associated with the sources can be compensated in real time. In this embodiment, the same microprocessor used for signal analysis would be well-suited for controlling the switching between signals as well as for servo gain control.

The frequency of switching between source monitoring and sample monitoring will depend on the time scales of the variations of the signal and the drifts of the sources. The optimal switching frequency is slower than the modulation frequency of the sources, yet faster than any variations of the sources or the sample. For example, if the technique were used in an application where the signal is modulated with the heart pulse (as in pulse oximetry) the switching frequency would be faster than that pulsatile frequency.

Spectrophotometer Embodiments

The above embodiments provide a measurement of a spectral derivative at a single wavelength. However, the technique described for the above embodiments is readily extendible to more than a single difference measurement.

A spectrophotometer is a device that measures an optical property, such as transmittance or reflectance, as a function of wavelength. Each of the embodiments described above can be applied in the form of a spectrophotometer by replacing its source assembly with sources that range, or can be tuned, over a broad wavelength range. When used in a spectrophotometer embodiment, a mathematical model or chemometric calibration and analysis of the raw spectra are typically used for extraction of concentration data.

Embodiment with 2N Fixed-Wavelength Sources

Figure 6:
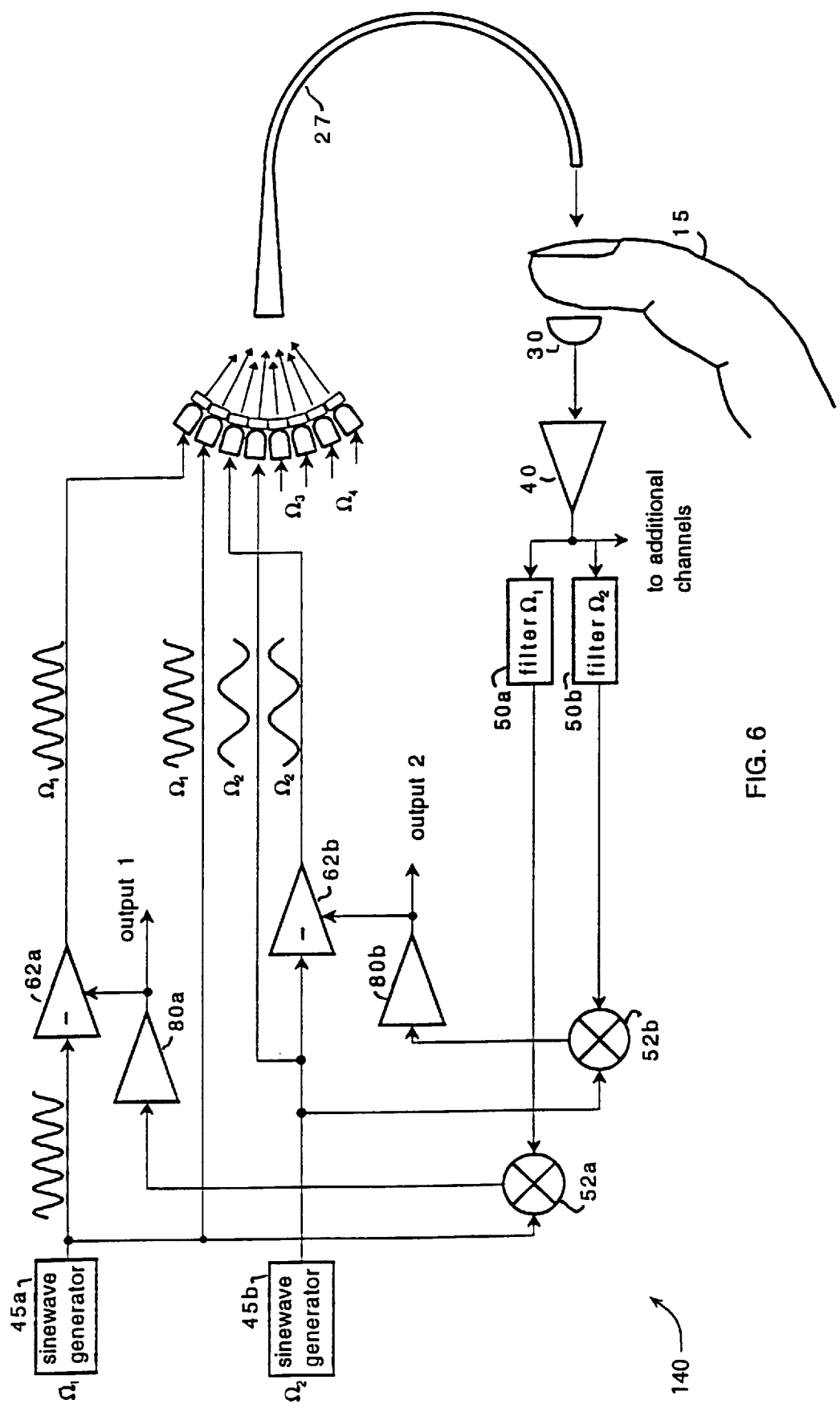
FIG. 6 is a schematic of an embodiment corresponding to that of FIG. 4, extended to provide N difference measurements through the use of 2N sources.

FIG. 6 is a schematic of a system 140 that extends system 90 of FIG. 4 to a system suitable for providing a plurality of N difference measurements. In most practical embodiments, N is unlikely to exceed 30–40, and is more likely to be less than about 10. In short, the system includes 2N sources (N pairs) and associated electronics for each pair. Each pair is modulated at a respective one of N fundamental frequencies. A single detector and preamplifier are used. This is a type of frequency division multiplexing and achieves simultaneous measurement at all wavelengths. The figure shows four such pairs of sources and the associated electronics for two of the sources. Elements corresponding to those in FIG. 4 have the same reference numerals, but the reference numerals for the replicated elements are provided with a letter suffix.

The spacing of the two wavelengths within a pair and the spacing of the N wavelength pairs from each other tend to be a function of the wavelength range of interest and the availability of sources. As a practical matter, it is not always possible to have the same wavelength spacing for all the pairs, nor is it always possible to uniformly span a wavelength range of interest.

Each of the N pairs of complementary sources is modulated at an independent one of the N fundamental electrical frequencies, and the combined light is homogenized and used to illuminate the sample. The Fourier component at each fundamental frequency is detected and provides a signal yielding one of the multiple difference measurements. When used with negative feedback all frequency components of the detected optical power are effectively nulled making the detected power virtually constant.

Irrespective of the number of sources, a single detector simultaneously measures all the signals at all the different fundamental frequencies. This approach provides for continuous monitoring of the measured quantity in real time through frequency division multiplexing.

Both sources of a given complementary pair are situated at nearby but distinct wavelengths. The signal from preamplifier 40 is filtered at N fundamental frequencies and each respective frequency component is demodulated using phase-sensitive detection. Each demodulated signal is fed back to suppress the contribution to the total optical power from its respective pair of sources. The measurements at the outputs of the servo amplifiers represent the spectral data at the mean wavelength of each complementary pair. For a large number of sources the spectrum approximates the first derivative spectrum.

Embodiment with (N+1) Fixed-Wavelength Sources

Figure 7:
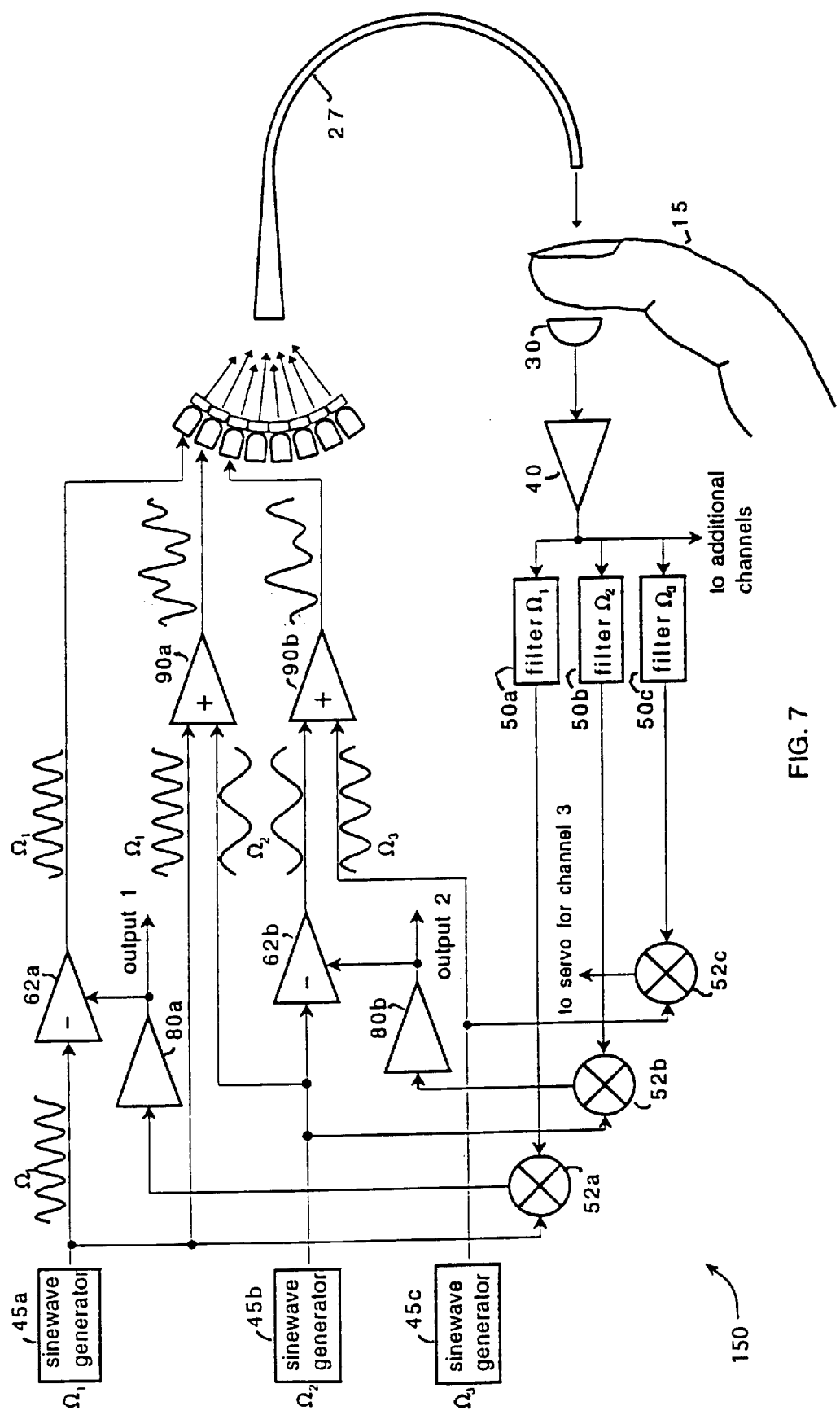
FIG. 7 is a schematic of an embodiment corresponding to that of FIG. 4, extended to provide N difference measurements through the use of (N+1) sources.

FIG. 7 is a schematic of a system 150 that extends system 90 of FIG. 4 to one that provides N difference measurements with only (N+1) sources. In this embodiment (N+1) sources at (N+1) generally evenly spaced wavelengths are used to measure a first derivative spectrum at N mean wavelengths. If the wavelength spacings are not uniform, the actual spacings can be used to calibrate the measured derivatives. If the wavelength spacings are highly non-uniform, the results will not yield derivatives, but will still contain useful spectral information.

Each source, excluding the first and last, is modulated at two fundamental electrical frequencies simultaneously. The signals from oscillators 45*a* and 45*b* are added electronically by a summing amplifier 90*ab*, the signals from oscillators 45*b* and 45*c* are added by a summing amplifier 90*bc*, etc., before driving their respective sources. As in the previous embodiments, one of each pair of modulation signals at a given frequency is inverted and modified by adjusting the output of inverting amplifiers 62*a* and 62*b*.

There are N fundamental frequencies $\Omega_1, \Omega_2, \ldots \Omega_N$. The figure shows circuitry for modulating the first source at fundamental frequency $\Omega_1$, the second source at fundamental frequencies $\Omega_1$ and $\Omega_2$, and the third source at fundamental frequencies $\Omega_2$ and $\Omega_3$. The last, or (N+1)th, source (not shown) is modulated only at the fundamental frequency $\Omega_N$. Also shown is the detection circuitry for three difference measurements and the servos for two of the measurements.

This approach uses one more than half the number of sources as the previous embodiment. Since a large part of the cost of such an instrument is in the source and filter assembly, a substantial cost can be saved in this configuration.

Embodiment with (N+1) Sources and Feedback before Sample

Figure 8:
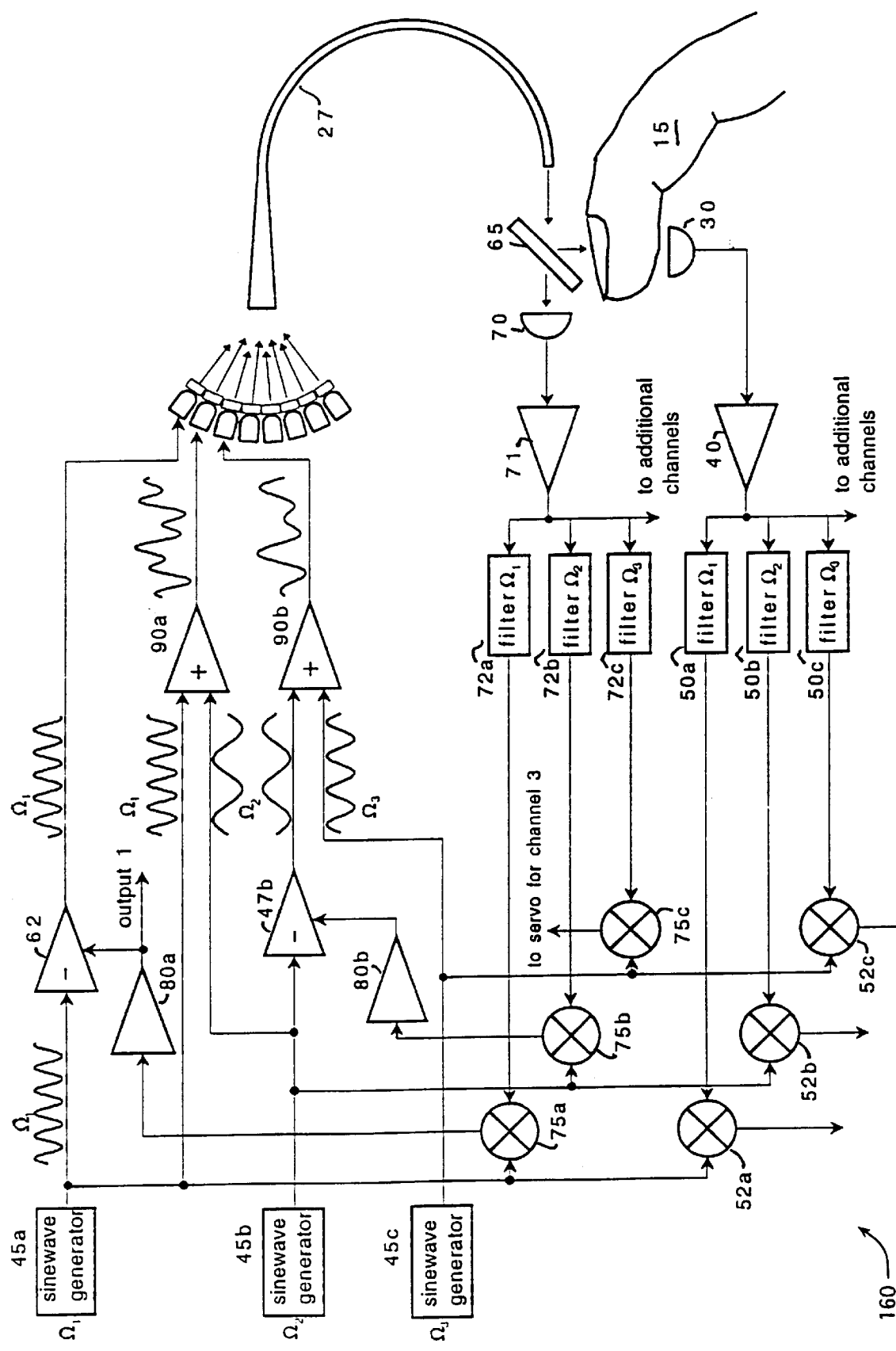
FIG. 8 is a schematic of an embodiment corresponding to that of FIG. 3, extended to provide N difference measurements through the use of (N+1) sources.

FIG. 8 is a schematic of a system 160 that extends system 60 of FIG. 3 to a system that provides N difference measurements using (N+1) sources.

Embodiment with (N+1) Fixed Sources and DSP

With the advent of optical disk technology, the huge home entertainment industry has driven down the costs for powerful signal processing electronic chips known as digital signal processors (DSP's). The economy and power of DSP's have spawned a secondary industry in computationally intensive instrumentation designed around the DSP chips.

All the circuitry shown schematically from signal detection to source modulation can be performed using a DSP, and most likely at a lesser cost than in the analog implementations shown above. A DSP can carry out the functions of: waveform generation, waveform mathematics, including mixing and differentiation, digital filtering, as well as servo control of the output waveforms that drive the sources or their amplitude modulators. A digital signal processor or a microprocessor can also perform the computationally intensive operations of data analysis, including the chemometric algorithms necessary to convert the raw spectral data to concentration measurements.

Figure 9:
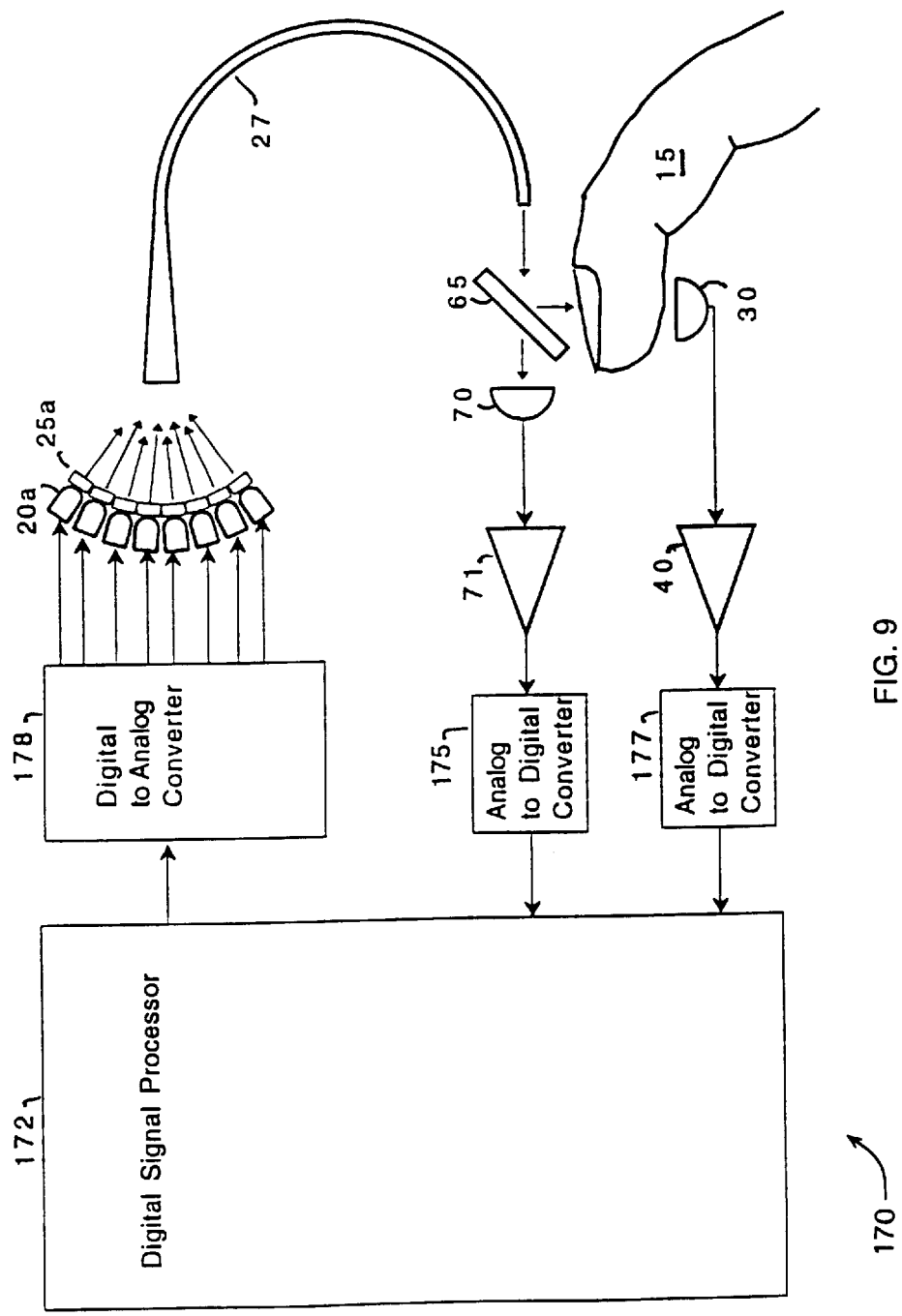
FIG. 9 is a schematic of a multi-wavelength embodiment with feedback utilizing a digital-signal-processor (DSP) chip (or other microprocessor) to perform all functions, including chemometrics, digitally.

FIG. 9 is a schematic of a system 170 using a DSP 172 for these functions. This is a variant of the system shown in FIG. 8. Two analog-to-digital converters (ADC's) 175 and 177 respectively transform the signals from preamplifiers 40 and 71 to digital signals used to provide data to DSP 172. The DSP also controls the modulation amplitudes of the sources by means of an array of digital-to-analog converters 178.

Embodiment with Tunable Source

A spectrometer based on the null-point detection technique using two tunable sources at closely-spaced wavelengths directly measures first derivative spectra. FIG. 10 shows an alternative tunable two-wavelength source assembly for providing a plurality of difference measurements with two sources. The tunable filter depicted in the figure is a graded circular interference filter 190 which is currently commercially available from Optical Coating Laboratories, Inc. (OCLI). Filter 190 is rotationally driven by a stepper motor 192 that is used to scan the spectrophotometer through the spectral range determined by the filter and the output range of the light sources. Typical graded interference filters might span the ranges of 400–1000 nm and 1000–2000 nm. A linearly graded filter may also be used, with a stepper motor that provides translational rather than rotational increments.

Not shown in the figure is the option of switching between different pairs of sources in order to extend the spectral wavelength range of the spectrophotometer. Alternatively, N+1 or 2N sources may be arranged around the filter with each source emitting light through a different region of the filter and hence at a different wavelength.

An alternative embodiment uses a pair of beams from a broadband source (visible or infrared) to illuminate two closely spaced portions of the graded filter to provide two closely spaced wavelengths. A beam chopper is used to modulate the two beams out of phase (one beam is illuminating its portion of the filter while the other beam is blocked). An optical encoder on the chopper is used to generate the reference electrical signal for phase-sensitive detection. As the stepper motor moves the graded filter, the beams illuminate different portions of the filter. By suitable selection of beam spacing and stepper motor increments, one can achieve measurements for desired wavelength separations over desired spectral regions.

Another alternative embodiment for the tunable light source uses a monochrometer with a diffraction grating. A pair of parallel input slits can be used to select and to superimpose the light at the two wavelengths upon a single output slit.

Alternative Subcomponent Embodiments

In any of the embodiments described above, the light sources can be independently amplitude modulated either internally or externally. For example, in the case of internal modulation, the output power of an LED or a laser diode can be modulated by modulating its drive current. Alternatively, the power from one or more sources can be modulated externally by means of an optical modulators, such as, for example, an electro-optic modulator, acousto-optic modulator, or liquid-crystal modulator.

An alternative mechanism of source modulation involves the modulation of the optical wavelength (or frequency) of a single source. For example, the center wavelength of the pass band of an interference filter can be altered by dithering the tilt angle of the filter slightly with respect to direction of beam propagation. Additional wavelength tuning methods include a birefringent filter and the use of a grating monochrometer as a narrow band-pass filter. In the latter case, dithering the angle of the diffraction grating by a small amount varies the center wavelength of its output beam. These methods yield phase-sensitive detection in a straightforward manner. Null-point detection is best achieved by modulating the source intensity in phase or out of phase with the wavelength dither.

The beam homogenizer depicted in FIGS. 1 and 3–9 is a tapered fiber-optic bundle optically coupled to a large single-core multimode fiber. Alternative beam homogenizers include integrating spheres and scattering media, such as ground glass substrates positioned between the source assembly and the sample. Certain applications for which the signals are strong compared with competing variations, such as measurement of oxygen saturation of hemoglobin as applied in pulse oximetry, may not require beam homogenization.

The mixer can be of the radio-frequency type, an analog multiplier, or its functions can be performed digitally by a DSP for embodiments using a DSP.

The most costly elements of the described spectrometer are likely to be the optical components. For example, typical 1994 prices are as follows. Narrow-pass interference filters cost $20 apiece, even a very low-grade grating monochrometer costs about $1000, a graded interference filter costs about $1000, and the detectors vary from $10 to $500, depending on the quality and wavelength range of interest. By comparison, the electronics are relatively inexpensive. The only electronic components of any substantial cost are the DSP microprocessor chips.

High Resolution Embodiment

This invention may also be extended to very high spectral resolution through the use of high-resolution sources, such as lasers. Specifically, two very nearly monochromatic lasers emitting wavelengths $\lambda$ and $\lambda+\delta\lambda$, where $\delta\lambda$ is very small (not necessarily greater than the respective source bandwidths) can be used as the sources. In this case, care must be taken so that the frequency of the amplitude modulation, $\Omega$, is less than $c/\delta\lambda$ so that additional sidebands are not created that will be detrimental to the spectral resolution of the device. All other aspects of this invention apply in this case without modification.

Conclusion

In conclusion, it can be seen that the present invention provides a powerful and inexpensive diagnostic tool for deriving spectral information at low noise and drift levels. A system according to the invention has the sensitivity of research-grade spectrophotometers at a small fraction the cost.

While the above is a complete description of specific embodiments of the invention, various modifications, alternative constructions, and equivalents may be used. Therefore, the above description should not be taken as limiting the scope of the invention as defined by the claims.

What is claimed:

1. Apparatus for measuring a difference between the value of an optical property of a sample at a first wavelength and the value of the optical property of the sample at a second wavelength, and a difference between the value of the optical property of the sample at the second wavelength and the value of the optical property of the sample at a third wavelength, the apparatus comprising:

first, second, and third optical sources emitting light at the first, second, and third wavelengths;

modulation means for modulating the optical power of each of said sources so that (a) the optical powers of said first and second sources have respective first and second components that vary periodically with a common frequency, wherein the periodic variation of said first component is of opposite sign to the periodic variation of said second component, and (b) the optical powers of said second and third sources have respective third and fourth components that vary periodically with an additional common frequency, wherein the periodic variation of said third component is of opposite sign to the periodic variation of said fourth component;

means for combining light from said first, second, and third sources and directing said light to engage the sample;

detection means, responsive to said light, so combined after engagement with the sample, for providing an electrical signal proportional to the total optical power of said light after engagement with the sample;

wherein said first and second components have substantially the same amplitude of power variation at said common frequency; and means, responsive to said electrical signal, for generating (a) an output signal proportional to the amplitude of a component of said electrical signal at said common frequency, whereupon said output signal is proportional to the difference between the value of the optical property of the sample at the first wavelength and the value of the optical property of the sample at the second wavelength, and (b) an additional output signal proportional to the amplitude of a component of said electrical signal at said additional common frequency, whereupon said additional output signal is proportional to the difference between the value of the optical property of the sample at the second wavelength and the value of the optical property of the sample at the third wavelength.

2. The apparatus of claim 1 wherein said means for generating an output signal comprises:

a bandpass filter for transmitting a filtered signal containing only frequencies in a range surrounding said common frequency.

3. The apparatus of claim 2 wherein said means for generating an output signal further comprises:

a phase-sensitive circuit coupled to an output from said bandpass filter for providing a DC signal proportional to the amplitude of said filtered signal.

4. The apparatus of claim 1, and further comprising:

control means, responsive to a signal at a control input, for changing the amplitude of power variation of said second component relative to said first component;

additional detection means, responsive to said light, so combined, before engagement with the sample, for providing an additional electrical signal proportional to the total optical power of said light before engagement with the sample; and means, responsive to said additional electrical signal for generating a control signal proportional to the amplitude of a component of said additional electrical signal at said common frequency and for communicating said control signal to said control input;

said control means responding to said control signal so as to minimize the amplitude of said component of said additional electrical signal at said common frequency, whereupon the amplitudes of power variation at said common frequency for said first and second sources are maintained substantially equal.

5. The apparatus of claim 1 wherein the average optical power of said first source and the average optical power of said second source are substantially equal.

6. The apparatus of claim 1 wherein said modulation means modulates said first and second sources with a waveform characterized by a fundamental frequency that is equal to said common frequency.

7. Apparatus for measuring a difference between the value of an optical property of a sample at a first wavelength and the value of the optical property of the sample at a second wavelength, and a difference between the value of the optical property of the sample at the second wavelength and the value of the optical property of the sample at a third wavelength, the apparatus comprising:

first, second, and third optical sources emitting light at the first, second, and third wavelengths;

modulation means for modulating the optical power of each of said sources so that (a) the optical powers of said first and second sources have respective first and second components that vary periodically with a common frequency, wherein the periodic variation of said first component is of opposite sign to the periodic variation of said second component, and (b) the optical powers of said second and third sources have respective third and fourth components that vary periodically with an additional common frequency, wherein the periodic variation of said third component is of opposite sign to the periodic variation of said fourth component;

means for combining light from said first, second, and third sources and directing said light to engage the sample;

detection means, responsive to said light, so combined, after engagement with the sample, for providing an electrical signal proportional to the total optical power of said light after engagement with the sample;

control means, responsive to a signal at a control input, for changing the amplitude of power variation of said first component relative to said second component;

additional control means, responsive to a signal at an additional control input, for changing the amplitude of power variation of said third component relative to said second component;

means, responsive to said electrical signal, for generating a control signal proportional to the amplitude of a component of said electrical signal at said common frequency and for communicating said control signal to said control input; and means, responsive to said electrical signal, for generating an additional control signal proportional to the amplitude of a component of said electrical signal at said additional common frequency and for communicating said additional control signal to said additional control input;

said control means responding to said control signal so as to minimize the amplitude of said component of said electrical signal at said common frequency, whereupon said control signal is proportional to the difference between the value of the optical property of the sample at the first wavelength and the value of the optical property of the sample at the second wavelengths;

said additional control means responding to said additional control signal so as to minimize the amplitude of said component of said electrical signal at said additional common frequency, whereupon said additional control signal is proportional to the difference between the value of the optical property of the sample at the second wavelength and the value of the optical property of the sample at the third wavelength.

8. The apparatus of claim 7 wherein said means for generating a control signal comprises:

a phase-sensitive circuit for providing a DC signal proportional to the amplitude of a component of said electrical signal at said common frequency; and a servo amplifier, responsive to said DC signal, for providing as said control signal an amplified version of said DC signal.

9. The apparatus of claim 8 wherein said means for generating a control signal further comprises:

a bandpass filter, coupled to said detection means, for transmitting to said phase-sensitive circuit a filtered signal containing only frequencies in a range surrounding said common frequency.

10. The apparatus of claim 7 wherein the average optical power of said first source and the average optical power of said second source are substantially equal.

11. The apparatus of claim 7 wherein said modulation means modulates said first and second sources with a waveform characterized by a fundamental frequency that is equal to said common frequency.

* * * * *